United States Patent [19]

Ausman et al.

[11] Patent Number: 4,792,449

[45] Date of Patent: Dec. 20, 1988

[54] METHOD FOR DRUG ADMINISTRATION

[75] Inventors: Robert K. Ausman, Long Grove, Ill.; Mark Adams; Gerado Caballero, both of Milwaukee, Wis.; Rahim Hamid, Wauwatosa, Wis.; Norman E. Hoffman, Wales, Wis.; Edward J. Quebbeman, Brookfield, Wis.; William J. Schulte, Wauwautosa, Wis.; Robert Thomson, New Berlin, Wis.; Julie Whipple, Milwaukee, Wis.; Steven D. Weitman, Irving, Tex.

[73] Assignee: Baxter Travenol Laboratories, Inc., Deerfield, Ill.

[21] Appl. No.: 7,890

[22] Filed: Jan. 28, 1987

[51] Int. Cl.$^4$ ............ A61K 9/68; A23D 5/00; A23G 3/00

[52] U.S. Cl. .................... 424/440; 426/613; 426/660

[58] Field of Search ............... 424/440; 426/613, 660

[56] References Cited

U.S. PATENT DOCUMENTS 4,609,543 9/1986 Morris et al. ............... 424/440

FOREIGN PATENT DOCUMENTS 2056 of 1855 United Kingdom ............... 424/440

OTHER PUBLICATIONS

Ota, B., "Administration of Cyclosporine", Transplantation Proceedings, vol. XV, No. 4, Suppl. 1 (Dec. 1983).

Kahan, B. D., Reid, M., and Newburger, J., "Pharmacokinetics of Cyclosporine in Human Renal Transplantation", Transplantation Proceedings, vol. XV, No. 1 (1983).

Schoenberg, L., Golden, D., Ota, B., Wideman, C., "Using Cyclosporine in Renal Transplantation", ANNA Journal, Oct. (1984).

Ptachcinski, R. J., Walker, S., Burckart, G. J., and Venkataramanan, R., "Stability and Availability of Cyclosporine Stored in Plastic Syringes", American Journal of Hospital Pharmacy, vol. 43, Mar. (1986).

*Primary Examiner*—Michael Lusignan
*Attorney, Agent, or Firm*—Marjorie D. Hunter; Susan Fentress; Paul C. Flattery

[57] ABSTRACT

This invention relates to a method for administering drugs. In particular a lipophilic drug is solubilized by a food, such as chocolate, and admixed with an oil-based carrier. The lipid soluble drug is thus conveyed to the gastrointestinal tract. Because this type of food is digested readily, the drug is absorbed as intended, and the dose is not subject to day-to-day variations.

11 Claims, No Drawings

METHOD FOR DRUG ADMINISTRATION

FIELD OF THE INVENTION

This invention relates to a method for administering drugs, involving solubilizing a drug in acceptable foods admixed with an oil. Because the food is digested readily, the drug is absorbed as intended, and the dose is not subject to day-to-day variations.

BACKGROUND OF THE INVENTION

Presently almost all forms of oral medication are manufactured in a form to be swallowed, thereafter to be dissolved within the lumen of the gasterointestinal tract and absorbed into the circulation whence it is distributed throughout the body. Occasionally, a suitable oral form is a liquid when it is swallowed, but to be sure a patient is receiving the entire dose of liquid medicine, often it must be coalesced with a diluent. In the instances the liquid medicine does not make a solution with a diluent that is agreeable to most people, there is considerable risk of day to day variation in dose received by the patient. When such a drug has a therapeutic dose and a toxic dose which are nearly equal, the disadvantage of the variation is enhanced, and the danger to the patient increased.

Some drugs, such as cyclosporine, are particularly difficult to administer. B. Ota, in an article entitled Administration of Cyclosporine, Transplantation Proceedings, Vol. XV, No. 4 Suppl. I. (December) 1983, points out that cyclosporine is soluble in alcohol and fat solvents, but not in acqueous solutions, thus making the administration of cyclosporine difficult. The article notes that because cyclosporine is fat soluble and dispensable in an oil base, it is considered quite distasteful by most patients.

In spite of mixing with chocolate milk, some patients vomited the liquid initially although later adapting to it and tolerating the drug for long term therapy. It is noted, however, that in one instance, the early nausea produced low blood levels and an early rejection episode. A convenient means of orally administering a lipophilic drug is therefore desirable.

SUMMARY OF THE INVENTION

This invention involves the use of a food, such as chocolate, which is palatable and into which drugs can be solubilized. The pharmaceutical agent is dissolved readily in the food which accepts drugs such as lipid soluble agents, permitting the patient to ingest fixed quantities of drug by eating standard amounts of the food. Because the food is digested readily, the drug is absorbed as intended, and the dose is not subject to day to day variation.

DETAILED DESCRIPTION OF THE INVENTION

The invention, in one exemplification, uses one of many forms of chocolate made into candy-bar-type sections to dissolve and then convey a lipophilic drug such as cyclosporine into the gastrointestinal tract. Chocolate typically contains a portion of oil along with other ingredients. In this embodiment, cyclosporine in olive oil is substituted for some of the regular portion of coconut oil. Chocolate does not require substantial heat for subsequent handling, so relatively heat-labile drugs can be submitted to this process.

After blending, which produces a homogenous mixture in which the drug is distributed evenly, the chocolate, or other food substance, is carried to completion and made in a form suitable for administration by molding. Packaging is employed which distinguishes the product from a regular food or candy. Different doses can be prescribed by making scoring marks in the chocolate.

Depending on the solubility characteristics of a chosen drug, a food can be selected which will form a solution which predictably will contain precise amounts of drug based on weight or volume. It is helpful if the food can be made into subsegments of various sizes in order to be able to alter the dose of drug with some ease.

To demonstrate even distribution throughout a batch of chocolate of beta hydroxy triptamine (BHT), a cyclosporine simulator, the BHT was mixed with chocolate, the mixture was made into wafers, and different portions of the wafers were analyzed to determine the concentration of BHT. As can be seen from the following tables, the BHT was evenly distributed throughout the wafers and the various portions of the wafers.

The invention can be utilized with any drug which can be incorporated into an oil base carrier. The vehicle for the oral drug can comprise sugar, cocoa butter, whole milk powder, chocolate liquor, lecithin, and vanillin, each in a range of from about 10% to 20%. Each constituent can be varied to some extent to achieve different tastes, consistencies or packaging, handling or storage characteristics. For cyclosporine, an olive oil solution in a concentration of 100 milligrams per milliliter is made for mixing with the vehicle. Doses of from about 25 mg to 500 mg are desirable for pediatric and adult use, the conventional adult dose being about 250 mg to 300 mg.

A suitable dosage would comprise 24 ml of a chocolate mixture vehicle of sugar, cocoa butter, whole milk powder, chocolate liquor, lecithin and vanillin, each in a range of from about 10% to 20%, and 6 ml of cyclosporine/olive oil for a total of 30 ml, to produce an equivalent one ounce chocolate bar.

EXAMPLE 1

CHOCOLATE AS A VEHICLE FOR THE DELIVERY OF LIPID SOLUBLE MEDICATIONS

Chocolate can serve as a vehicle for delivery of some potent lipid soluble medications that are presently only available in liquid forms because it has the advantage of easy divisibility to accomodate a wide range of dosages and pleasant taste to enhance compliance.

This example demonstrates that a lipid soluble drug will form homogeneous mixture when mixed in chocolate. Butylated hydroxytoluene (BHT) was the "drug" used due to its simple chemical nature, complete solubility in olive oil, nontoxic nature, and ease of analysis using HPLC.

MATERIALS AND METHODS

A known amount of BHT was mixed into a 5 pound lot of milk chocolate. Thirty-two (32) grams of BHT were dissolved in 253 grams of olive oil. The chocolate/BHT/olive oil mixture was then formed into approximately 20 gram bars which were assayed for BHT content by dividing a bar into sixteen pieces and assaying each piece. Pieces of nine randomly chosen bars also were measured to determine BHT. The two methods of measurement demonstrated a homogeneous mixture within a single bar and also from bar to bar.

Assays were done by the HPLC method. Each sample of chocolate to be assayed was first dissolved in 5 ml of ethyl ether. Acetonitrile was added to bring the volume to 20 ml. A 100 microliter aliquot was taken and brought to a volume of 20 ml with acetonitrile. This dilution was assayed by the HPLC method. BHT standards were run before each batch.

RESULTS

The range of BHT concentration in the single bar divided into sixteen pieces was 12.7 to 13.7 mg/gram. The mean was 13.2, standard deviation 0.300832 and standard error 0.075208. The BHT range between the nine randomly chosen bars was 13.5 to 13.7 mg BHT per gram chocolate. The mean was 13.6, standard deviation 0.09718 and standard error 0.0322942.

TABLE NUMBER ONE
CONCENTRATION OF BHT IN A SINGLE BAR OF CHOCOLATE
UNITS - MG BHT PER GRAM OF CHOCOLATE

| 1 | 2 | 3 | 4 |
|---|---|---|---|
| 5 | 6 | 7 | 8 |
| 9 | 10 | 11 | 12 |
| 13 | 14 | 15 | 16 |

| | | | | | | | | |
|---|---|---|---|---|---|---|---|---|
| POSITION # | 1 | 2 | 3 | 4 | 5 | 6 | 7 | 8 |
| WEIGHT (GM) | .93 | 1.30 | 1.17 | 1.12 | 1.08 | 1.09 | 1.10 | 1.07 |
| BHT CONC (MG BHT/ GM CHOC) | 13.7 | 13.2 | 12.8 | 12.6 | 13.3 | 13.4 | 13.4 | 13.2 |
| POSITION # | 9 | 10 | 11 | 12 | 13 | 14 | 15 | 16 |
| WEIGHT (GM) | .90 | 1.05 | .92 | 1.04 | .94 | 1.19 | 1.01 | 1.01 |
| BHT CONC MG BHT/ GM CHOC | 13.4 | 13.2 | 12.6 | 13.3 | 13.4 | 13.3 | 13.2 | 13.4 |

N = 16 SUM 211.4 MEAN 13.2 T VALUE 2.13 +/−.160 STD DEV .301
COEFFICIENT OF VARIATION = 2.28%

TABLE NUMBER TWO
CONCENTRATION OF BHT IN RANDOMLY CHOSEN BARS (N = 9)
SAMPLING SITE WAS ROTATED IN EACH BAR

| 1 | 2 | 3 |
|---|---|---|
| 4 | 5 | 6 |
| 7 | 8 | 9 |

| | | | | | | | | | |
|---|---|---|---|---|---|---|---|---|---|
| BAR # | 1 | 2 | 3 | 4 | 5 | 6 | 7 | 8 | 9 |
| SITE # | 1 | 2 | 3 | 4 | 5 | 6 | 7 | 8 | 9 |
| WEIGHT(GM) | .73 | .83 | 1.02 | .79 | .79 | .76 | .86 | .77 | .76 |
| CONC BHT MG BHT/GM CHOC | 13.8 | 13.6 | 13.7 | 13.5 | 13.6 | 13.6 | 13.6 | 13.5 | 13.7 |

N = 9 SUM 122.6 T VALUE 2.31 +/−.075 STD DEV .097
COEFFICIENT OF VARIATION = 0.71%

What is claimed is:

1. A method for providing a drug to a patient in a form suitable to be swallowed by the patient, where the drug is lipid soluble, but not water soluble, comprising the steps of:
   a. dissolving the drug in a lipid solution; and
   b. dissolving the resulting drug-lipid solution in liquid, candy-grade chocolate.

2. The method according to claim 1 and further comprising the steps of:
   a. determining the volume of the drug-lipid solution; and
   b. removing a volume of coconut oil from the chocolate equal to the volume of the drug-lipid solution prior to dissolving the drug-lipid solution in the chocolate.

3. A method for providing a drug to a patient in a form suitable to be swallowed by the patient, where the drug is lipid soluble, but not water soluble, comprising the steps of:
   a. dissolving the drug in olive oil; and
   b. dissolving the resulting drug-olive oil solution in liquid, candy-grade chocolate.

4. The method according to claim 3 and further comprising the steps of:
   a. determining the volume of the drug-olive oil solution; and
   b. removing a volume of coconut oil from the chocolate equal to the volume of the drug-olive oil solution prior to dissolving the drug-olive oil solution in the chocolate.

5. A method for providing a cyclosporine drug to a patient in a form suitable to be swallowed by the patient, comprising the steps of:
   a. dissolving the cyclosporine drug in a lipid solution; and
   b. dissolving the resulting cyclosporine-lipid solution in chocolate.

6. The method according to claim 5 and further comprising the steps of:
   a. determining the volume of the cyclosporine-lipid solution; and
   b. removing a volume of coconut oil from the chocolate equal to the volume of the cyclosporine-lipid solution prior to dissolving the cyclosporine-lipid solution in the chocolate.

7. A method for providing a cyclosporine drug to a patient in a form suitable to be swallowed by the patient, comprising the steps of:
   a. dissolving the cyclosporine drug in olive oil; and
   b. dissolving the resulting cyclosporine-olive oil solution in chocolate.

8. The method according to claim 7 and further comprising the steps of:
   a. determining the volume of the cyclosporine-oil solution; and
   b. removing a volume of coconut oil from the chocolate equal to the volume of cyclosporine-olive oil solution prior to dissolving the cyclosporine-olive oil in the chocolate.

9. A drug dosage form of a candy-bar type consisting of cyclosporine dissolved in olive oil, said cyclosporine-olive-oil mixture being blended with a suitable vehicle including liquid, candy grade chocolate to produce a homogenous mixture in which the cyclosporine is distributed evenly throughout the chocolate in the bar.

10. The drug dosage form of claim 9 including from about 25 milligrams to about 500 milligrams of cyclosporine.

11. The drug dosage form of claim 10 wherein the vehicle includes sugar, cocoa butter, whole milk powder, chocolate liquor, lecithin and vanillin, each in the range of from about 10% to 20% of the total.

* * * * *